US008512376B2

(12) United States Patent
Thornes

(10) Patent No.: US 8,512,376 B2
(45) Date of Patent: Aug. 20, 2013

(54) METHOD AND APPARATUS FOR INTERNAL FIXATION OF AN ACROMIOCLAVICULAR JOINT DISLOCATION OF THE SHOULDER

(75) Inventor: Brian Thornes, Dublin (IE)

(73) Assignee: Arthrex, Inc., Naples, FL (US)

( * ) Notice: Subject to any disclaimer, the term of this patent is extended or adjusted under 35 U.S.C. 154(b) by 1839 days.

(21) Appl. No.: 11/482,038

(22) Filed: Jul. 7, 2006

(65) Prior Publication Data

US 2007/0016208 A1    Jan. 18, 2007

Related U.S. Application Data

(63) Continuation-in-part of application No. 10/233,122, filed on Aug. 30, 2002, now Pat. No. 7,235,091.

(60) Provisional application No. 60/697,125, filed on Jul. 7, 2005.

(51) Int. Cl.
*A61B 17/04* (2006.01)

(52) U.S. Cl.
USPC ............................................................ 606/232

(58) Field of Classification Search
USPC ................ 606/213, 232; 623/13.14, 232
See application file for complete search history.

(56) References Cited

U.S. PATENT DOCUMENTS

| 2,765,787 | A | * | 10/1956 | Pellet | 623/23.27 |
| 4,988,351 | A | * | 1/1991 | Paulos et al. | 606/232 |
| 5,211,647 | A | * | 5/1993 | Schmieding | 606/104 |
| 5,219,359 | A | * | 6/1993 | McQuilkin et al. | 606/232 |
| 5,306,290 | A | * | 4/1994 | Martins et al. | 606/232 |
| 5,409,490 | A | * | 4/1995 | Ethridge | 606/80 |
| 2003/0130694 | A1 | * | 7/2003 | Bojarski et al. | 606/228 |
| 2004/0236373 | A1 | * | 11/2004 | Anspach, III | 606/232 |

OTHER PUBLICATIONS

Su et al., Using Suture Anchors for Corococlavicular Fixation in Treatment of Complete Acromioclavicular Separation, May 2004, The American Journal of Orthopedics, pp. 256-257.*
Edwin P. Su, et al., "Using Suture Anchors for Coracoclavicular Fixation in Treatment of Complete Acromioclavicular Separation", *The American Journal of Orthopedics*, May 2004.

* cited by examiner

*Primary Examiner* — Corrine M McDermott
*Assistant Examiner* — Christina Lauer
(74) *Attorney, Agent, or Firm* — Dickstein Shapiro LLP

(57) ABSTRACT

An apparatus and method for surgically reducing and internally fixing a shoulder acromioclavicular joint dislocation are disclosed. The apparatus preferably comprises a button and a washer, the washer being flexibly secured to the coracoid process of the scapula by means of a bone screw, the button and washer being secured together by means of a first suture. A second suture is provided secured between the button and a needle, such that the needle and associated button, may be advanced through a hole drilled through the clavicle, wherein the button and the washer may then be tightened, reducing the coracoclavicular distance, by means of the first suture connected therebetween, to reduce and hold a desired acromioclavicular joint dislocation.

13 Claims, 8 Drawing Sheets

METHOD AND APPARATUS FOR INTERNAL FIXATION OF AN ACROMIOCLAVICULAR JOINT DISLOCATION OF THE SHOULDER

This application claims the benefit of U.S. Provisional Application Ser. No. 60/697,125 filed on Jul. 7, 2005, the entire disclosure of which is incorporated by reference. This application is also a continuation-in-part of application Ser. No. 10/233,122 filed Aug. 30, 2000, now U.S. Pat. No. 7,235,091, which in turn claims priority under 35 U.S.C. §119 to IE S2002/0504 filed Jun. 20, 2002.

FIELD OF THE INVENTION

The present invention relates to an apparatus and a method for internal fixation of an acromioclavicular joint dislocation of the shoulder with resultant superior migration of the lateral end of the clavicle with respect to the acromium and the coracoid of the scapula.

BACKGROUND OF THE INVENTION

Acromioclavicular ("AC") joint dislocations are characterized by severe upward displacement of the lateral end of the clavicle relative to the acromium of the scapula. Surgery is recommended to reduce and internally fix the displacement, which could otherwise lead to a painful deformity and loss of function.

This invention relates to reconstruction surgery and particularly to reconstruction surgery for Rockwood types II-VI AC joint dislocations of the shoulder (Rockwood, Williams, & Young, *Injuries to the Acromioclavicular Joints*, in FRACTURES IN ADULTS 1341-1413 (Rockwood & Green, eds., 3$^{rd}$ ed., 1996)). More particularly, the invention relates to the use of a first suture anchor-suture-second suture anchor technique to reduce and internally fix the dislocation between the clavicle and the coracoid process.

Injuries to the AC joint are generally classified as types I-VI, depending on the type and amount of disruption to the AC and the coracoclavicular ligaments. A type III AC dislocation of the shoulder is a common injury that occurs primarily from having a fall to the point of the shoulder. A type III injury is characterized by disruption of the AC and coracoclavicular ligaments, the dislocation of the AC joint and the upward relative displacement of the lateral end of the clavicle. The coracoclavicular interspace is greater than in the normal shoulder.

There are presently two basic treatment options available: non-operative treatments and operative procedures.

The non-operative option includes external, closed reduction. Various external, closed reduction procedures have been tried in the past using straps, casts, and different taping techniques. Generally, it has been believed that the procedures would work if applied continuously. Unfortunately, it has been found not to work as no one can wear them continuously because of skin breakdown and discomfort. As a result, such treatment regimes rarely have been successful. The patient must inevitably accept a cosmetic deformity and suffer from pain and fatigue after prolonged physical activity or heavy lifting.

Operative treatments to date have focused on open reduction and direct repair or reconstruction of the ligaments. This procedure corrects the deformity and is generally accepted as providing the best results. However, this usually entails an extensive open operation. The deltoid and trapezius muscles are taken off the clavicle and dissected to expose the underside of the clavicle and the coracoclavicular ligaments and the coracoid process. The procedure requires an in-hospital stay, extended time for the surgical wound to heal, and rehabilitation. The open reduction procedure is generally recommended as the treatment of choice for people involved in heavy lifting work or active athletics. The remaining population is generally told to accept the deformity and to accept the pain and fatigue after heavy lifting or activity.

It is well-known in the art to fix the coracoclavicular space by drilling a hole through the clavicle and into the coracoid process and by then inserting a screw (a Bosworth screw, for example) therebetween. It is also well-known to loop a flexible coupling such as a nylon tape around both the coracoid and the clavicle and to knot them together. This has the disadvantage of requiring that all of the coracoid be exposed. It is also known to drill a hole in the coracoid process and attach a single suture anchor, with a pair of sutures extending therefrom, into the coracoid. The free ends of the sutures are then looped about the clavicle and tied to each other.

Non-operative treatment options generally provide unacceptable results. The open reduction treatment, while providing generally good results, has the disadvantage of an in-hospital stay plus the extensive time required for healing and rehabilitation. A surgical outpatient technique that would correct the deformity and allow healing of the injury in a normal anatomic position without extensive tissue dissection and less scarring would provide a substantial improvement over current treatment methods.

It is an object of the present invention to overcome the problems associated with the prior art, whilst permitting normal physiological movement of the clavicle relative to the coracoid.

BRIEF SUMMARY OF THE INVENTION

The present invention relates to a surprising use of a first suture anchor-suture-second suture anchor technique. The proposed method of the present invention is simple and is performed by a mini-open approach.

In a first aspect of the present invention there is provided an apparatus for use in internal fixation of AC joint dislocations of a shoulder. The apparatus of the first aspect of the present invention is a kit of parts for internal fixation of an AC joint dislocation of a shoulder, the shoulder including a clavicle, a coracoid process and an acromium, the kit of parts comprising a first suture anchor; a second suture anchor, the first and second suture anchors being adapted for engagement in or on the clavicle and the coracoid process, respectively; a flexible coupling mountable, in use, between the first and second suture anchors; and a needle releasably securable to at least one of the first and second suture anchors, in which the first and second suture anchors each have at least first and second apertures and the flexible coupling is a first suture which is double looped through the first and second suture anchors.

Preferably, the first suture is fed, in use, through a first aperture of the second suture anchor, and through, in turn, the second and first apertures of the first suture anchor and through, in turn, second and first apertures of the second suture anchor, and through, in turn, the second and first apertures of the first suture anchor and through the second aperture of the second suture anchor.

Preferably, the first suture anchor comprises a button and the second suture anchor comprises a washer, the washer being adapted and dimensioned to engage with a bone anchor. Alternatively, each of the first and second suture anchors can be a button. In another embodiment, each of the first and second suture anchors can be a washer, the washer being adapted and dimensioned to engage with a bone anchor. In yet another embodiment, the first suture anchor is a washer and the second suture anchor is a button. The bone anchor may be a bone screw, a bone nail, a bone staple or an intraosseous bone anchor. A bone screw is preferred. Even more preferably, the washer has a central aperture and at least two, preferably at least four, peripheral apertures, the central aperture being adapted and dimensioned to accept a bone screw.

More preferably, the first suture anchor is a button having an oblong body and first and second apertures and the second suture anchor is a washer adapted to engage with a bone anchor and having at least two, preferably at least four, peripheral apertures. In this embodiment, the first suture is fed through a first peripheral aperture of the washer and through, in turn, the second and first apertures of the button and through, in turn, second and third peripheral apertures of the washer, and through, in turn, the second and first apertures of the button and through the fourth peripheral aperture of the washer. A loop is formed on the underneath of the washer, by the path of the first suture between the second and third peripheral apertures. If desired, the free ends of the first suture may be fed under this loop, to provide a self-tightening suture.

When one or both of the suture anchors is a button, the needle is preferably secured to one or both of the first and second buttons by means of a second suture looped through one of the first or second apertures of the first and/or second buttons, the second suture being operatively associated with the needle.

In a second aspect of the present invention there is provided a method for internal fixation of AC joint dislocations. The method of the present invention comprises the steps of providing an apparatus according to the first aspect of the present invention; securing the first and second suture anchors on or adjacent the clavicle and the coracoid process, respectively; and reducing and fixing the distance between the clavicle and the coracoid process, by traction of the flexible coupling.

When the apparatus of the first aspect of the invention comprises a button as the first suture anchor and a washer as the second suture anchor, the method preferably comprises the steps of drilling a clavicle hole through the clavicle and a coracoid hole into the coracoid process; passing the needle through the clavicle hole, so as to advance the button longitudinally through the clavicle hole; pivoting the button so as to engage the button against a superior surface of the clavicle; inserting a screw through a central aperture of the washer into the coracoid hole in a superior aspect of the coracoid process; and reducing and fixing the distance between the clavicle and the coracoid process, by traction of the flexible coupling. Preferably, the needle is uncoupled from the button when the button has been advanced through the clavicle hole and has engaged against the superior surface of the clavicle.

It will be appreciated by those skilled in the art that traction of the flexible coupling can be effected by hand traction or by the use of a suture tensioner. Suitable suture tensioners are well known in the art.

In a third aspect of the present invention there is provided a button for use in the apparatus of the first aspect of the invention and for use in the method of the second aspect of the present invention. The button of the third aspect of the invention can be used as either the first or second suture anchor or as each of the first and second suture anchors. The button of the third aspect of the present invention may comprise an oblong body defining first and second apertures. Preferably, each of the first and second apertures is oblong, their longitudinal mid-lines being located substantially about a longitudinal mid-line of the oblong body.

Alternatively, each of the first and second apertures is substantially triangular in plan view. In this alternative embodiment, each aperture is tapered and terminates in an apex, the apices being directed away from each other. Preferably, each of the apertures comprises first, second and third walls and the first walls of the respective first and second apertures are substantially parallel.

The button of the third aspect of the present invention may have any suitable dimension (width, length and thickness). If the button is oblong, for example, the button of the third aspect of the present invention can have a width of 2.5 mm to 4.0 mm without compromising implant strength, although a width of 3.0 mm to 4.0 mm is preferred. The length of the button of the third aspect of the present invention is less critical but may, for example, be in the range 7.5 mm to 12.5 mm. A length in the range 9 mm to 11 mm is preferred since the button of the third aspect of the present invention is then slightly less palpable under the skin following implantation.

Each of the first and second apertures of the button of the third aspect of the present invention may have any shape or geometry. For example, one embodiment is an aperture which is substantially triangular in plan view. Another embodiment is an egg-shaped or oval aperture, the curved narrower end comprising the apex.

In a fourth aspect of the present invention there is provided a washer for use in the apparatus of the first aspect of the invention and for use in the method of the second aspect of the present invention. The washer of the fourth aspect of the invention can be used as either the first or second suture anchor or as each of the first and second suture anchors. The washer of the fourth aspect of the present invention comprises a body adapted for engagement with a bone anchor and having at least two, preferably at least four, peripheral apertures. The washer of the fourth aspect of the present invention optionally comprises a disc-shaped body defining a central aperture shaped and dimensioned to accept a bone screw and having four peripheral apertures. Preferably, each of the central and peripheral apertures is circular in plan view.

The washer of the fourth aspect of the present invention can have an external diameter of 6.5 mm to 13.0 mm and a thickness of 1.0 mm to 2.0 mm without compromising implant strength, although an external diameter of 8 mm to 12 mm and a thickness of about 1.5 mm is preferred. The central aperture of the washer of the fourth aspect of the present invention can have an internal diameter of 2.5 mm to 6.5 mm, although an internal diameter of 3.5 mm to 5.5 mm is preferred. In an optional embodiment, the four peripheral apertures of the washer of the fourth aspect of the present invention can have an internal diameter of 0.5 mm to 2.0 mm, although an internal diameter of 0.8 mm to 1.2 mm is preferred.

As used herein, the term "button" or "washer" is intended to mean any suitably shaped and dimensioned suture anchor or stress bearing member which is capable of transmitting a force incident thereon to any body with which the button or washer is in contact.

BRIEF DESCRIPTION OF THE DRAWINGS

These and other features and advantages of the invention will be more apparent from the following detailed description that is provided in connection with the accompanying drawings and illustrated exemplary embodiments of the invention, in which.

DETAILED DESCRIPTION OF THE INVENTION

Figure 1:
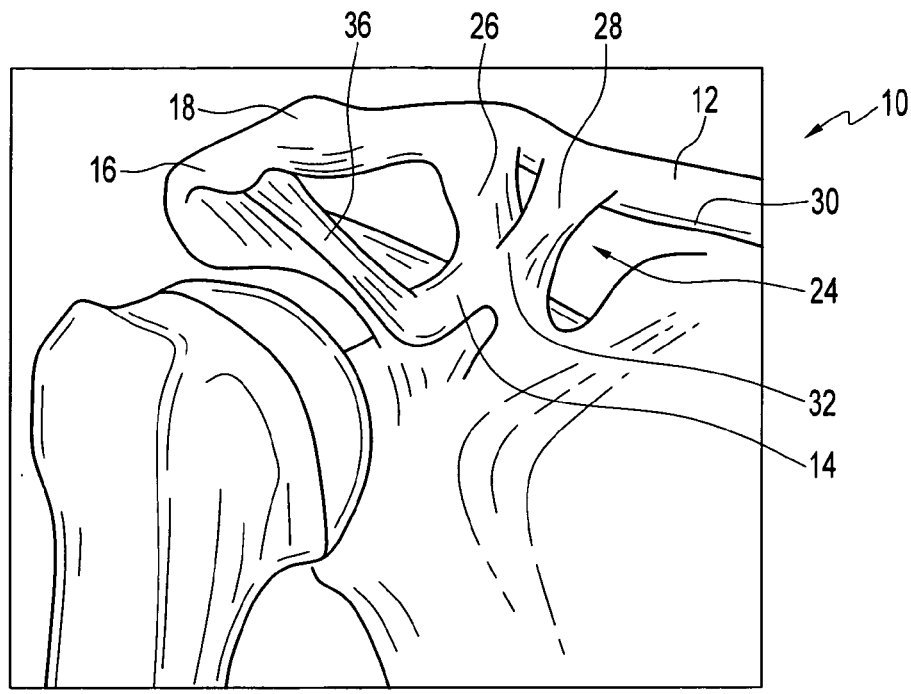
FIGS. 1 and 1a show an anterior view and a schematic view, respectively, of a normal acromioclavicular joint.

In the following detailed description, reference is made to the accompanying drawings, which form a part hereof and illustrate specific embodiments in which the invention may be practiced. In the drawings, like reference numerals describe substantially similar components throughout the several views. These embodiments are described in sufficient detail to enable those skilled in the art to practice the invention, and it is to be understood that other embodiments may be utilized, and that structural, logical and electrical changes may be made without departing from the spirit and scope of the present invention.

The present invention provides minimally invasive, flexible fixation of the AC joint dislocation by resisting superior migration of the clavicle with respect to the coracoid process. It allows physiological micromotion at the AC joint. There should be no need for routine removal of the implant.

The present invention is indicated for use in the fixation of AC joint dislocation. These are typically seen in Rockwood type III AC joint dislocations, usually caused by severe downward blunt trauma to the point of the shoulder, or acromium. Typically, the clavicle is upwardly displaced as a result of the injury because of disruption to the AC and coracoclavicular ligaments. Reduction and fixation of displaced AC joint dislocations are necessary to prevent painful deformity and loss of function.

Figure 2:
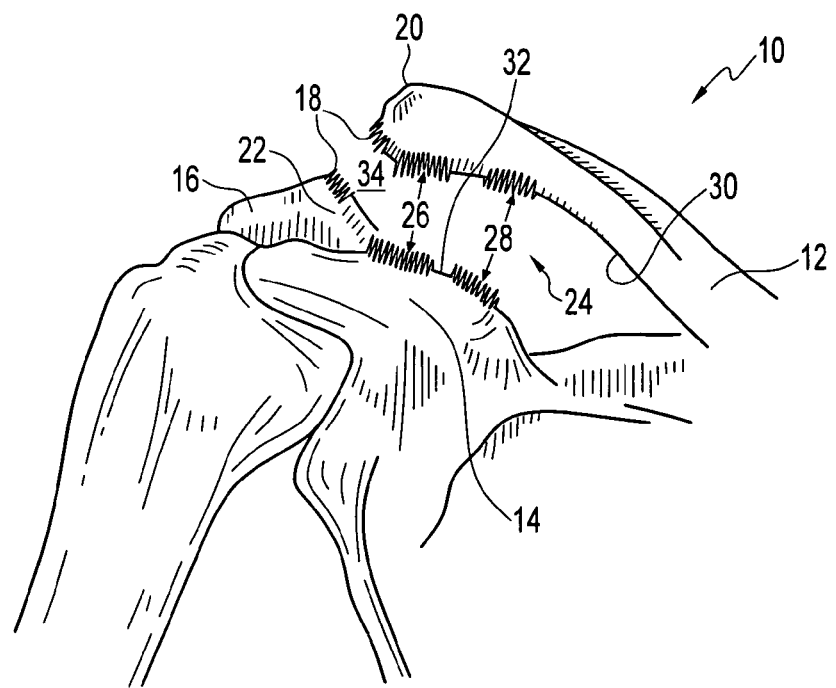
FIGS. 2 and 2a show an anterior view and a schematic view, respectively, of a Rockwood Type III acromioclavicular joint dislocation, with superior migration of the clavicle with respect to the acromium.
Figure 1A:
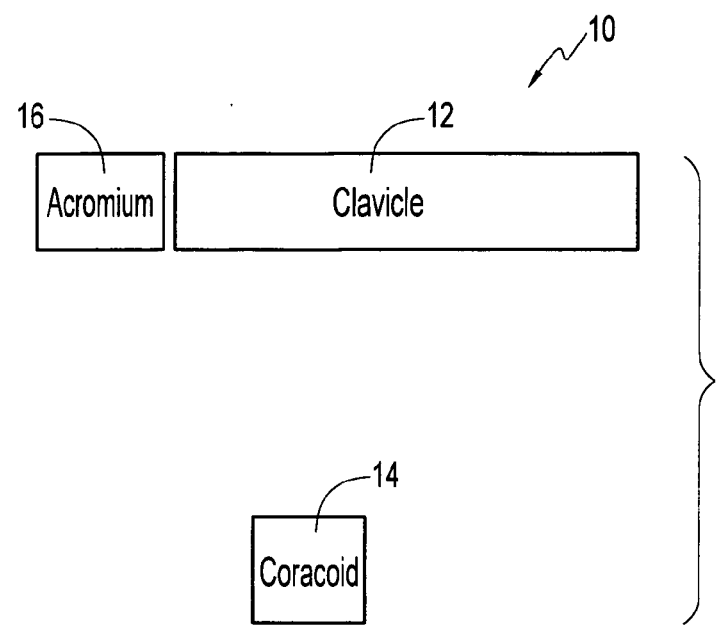
Figure 2A:
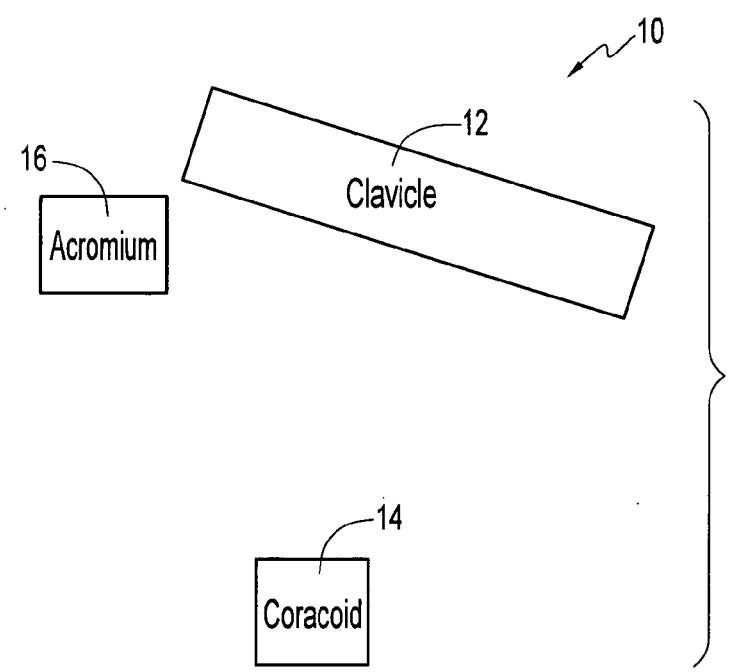

FIGS. 1 and 1a show anterior and schematic views of a normal shoulder 10. FIGS. 2 and 2a show anterior and schematic views of a shoulder 10 that has suffered a Rockwood type III AC joint dislocation injury.

Referring to FIGS. 1 and 2, the structure of a shoulder 10 relevant to a Rockwood type III dislocation injury includes the clavicle 12, the coracoid process 14 and the acromium 16. The acromium 16 and the clavicle 12 are connected by the acromioclavicular ligament 18. The acromioclavicular ligament 18 extends from the lateral end 20 of the clavicle 12 to the medial surface 22 of the acromium 16. The coracoid process 14 is connected to the clavicle 12 by the coracoclavicular ligaments 24, which comprise the trapezoid ligament 26 and the conoid ligament 28. The coracoclavicular ligaments 24 extend from the inferior surface 30 of the clavicle 12 to the superior surface 32 of the coracoid process 14.

A Rockwood type III AC joint dislocation is characterized by the disruption of the AC and the coracoclavicular ligaments 18, 24, respectively. As shown in FIGS. 2 and 2a, the clavicle 12 separates from, and moves away from, the coracoid process 14 and the acromium 16, accompanied by disruption of the coracoclavicular and the AC ligaments 18, 24, respectively. The acromioclavicular joint 34 (FIG. 2) is dislocated and the clavicle 12 is relatively displaced upwardly. The coraco-acromial ligament 36 (FIG. 1) is not impacted in the type III shoulder dislocation.

Repair of the type III shoulder dislocation according to the present invention is an out-patient procedure performed with a general anesthetic. The procedure is done with the patient lying supine on the operating table, preferably in the "deck-chair" position to allow the surgeon full access to the affected shoulder.

Figure 3:
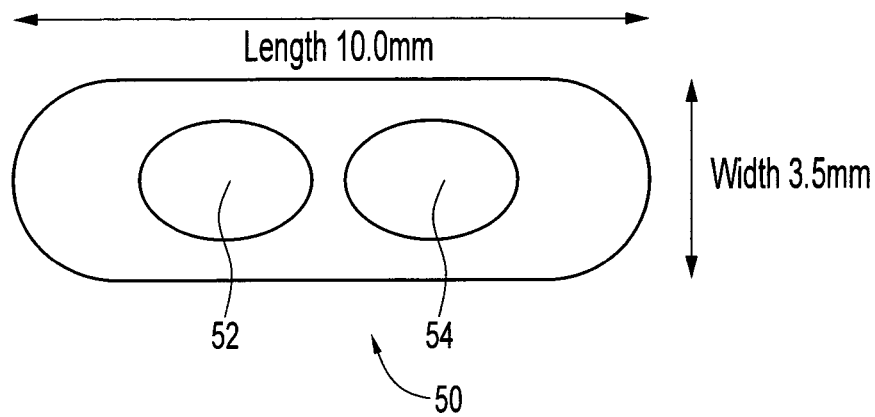
FIG. 3 shows a plan view of a first or second suture anchor in the form of a button of the present invention.

Referring to FIG. 3, the apparatus of the present invention comprises a first or second suture anchor in the form of a button 50, which, in the embodiment illustrated, is about 10.0 mm in length by about 3.5 mm in width. The button 50 is preferably formed from titanium or stainless steel, although it will be appreciated that any other suitable material could be used, in particular any suitable bioabsorbable material. The button 50 has a first aperture 52 and a second aperture 54 which, in the embodiment illustrated, are oblong in shape, the longitudinal mid-line of each of the first and second apertures 52, 54 being located substantially about a longitudinal mid-line of the button 50.

Figure 4:
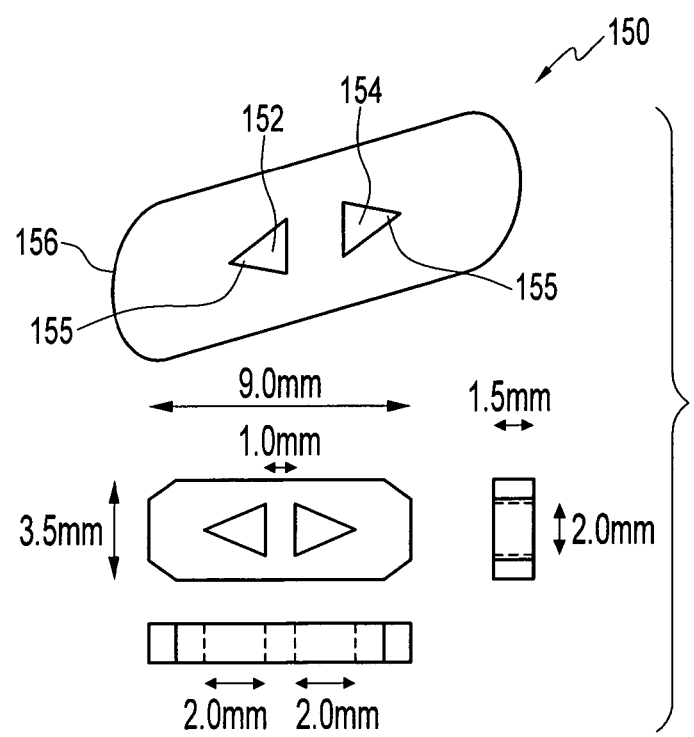
FIG. 4 shows perspective, plan and sectional view of an alternative embodiment of a button according to the invention.

Referring to FIG. 4, there is illustrated an alternative first or second suture anchor, generally indicated as 150. In the illustrated alternative embodiment, the button 150 is about 9.0 mm in length by about 3.5 mm in width, with a thickness of about 1.5 mm. The button 150 has first and second apertures 152 and 154, respectively. In the illustrated alternative embodiment, each of the apertures 152, 154 are triangular in shape, the respective apices 155 being directed away from each other and being located substantially about a longitudinal mid-line of the button 150.

Figure 5:
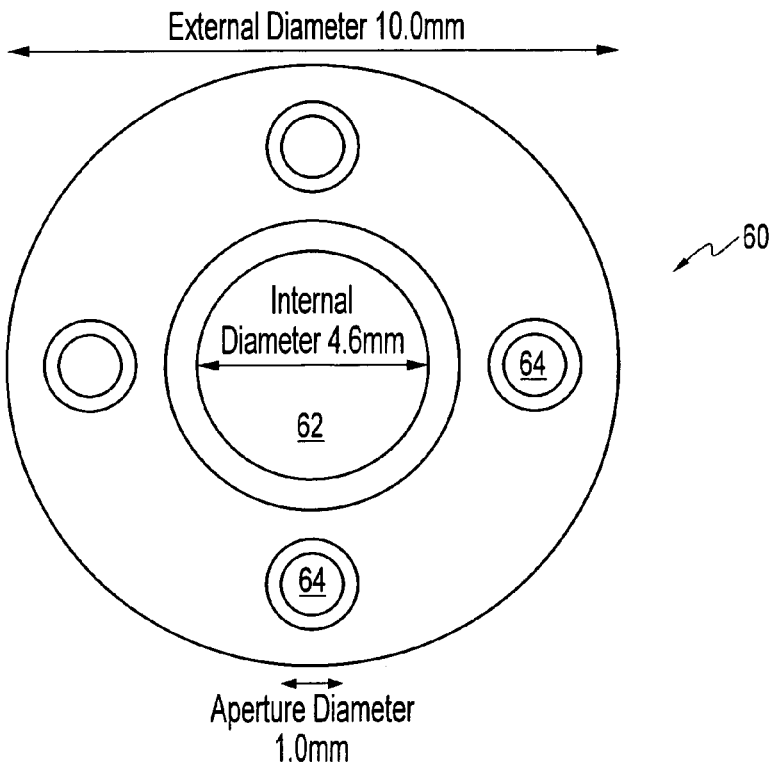
FIGS. 5 and 5a show a plan and an undersurface view, respectively, of a first or second suture anchor in the form of a washer of the present invention.
Figure 5A:
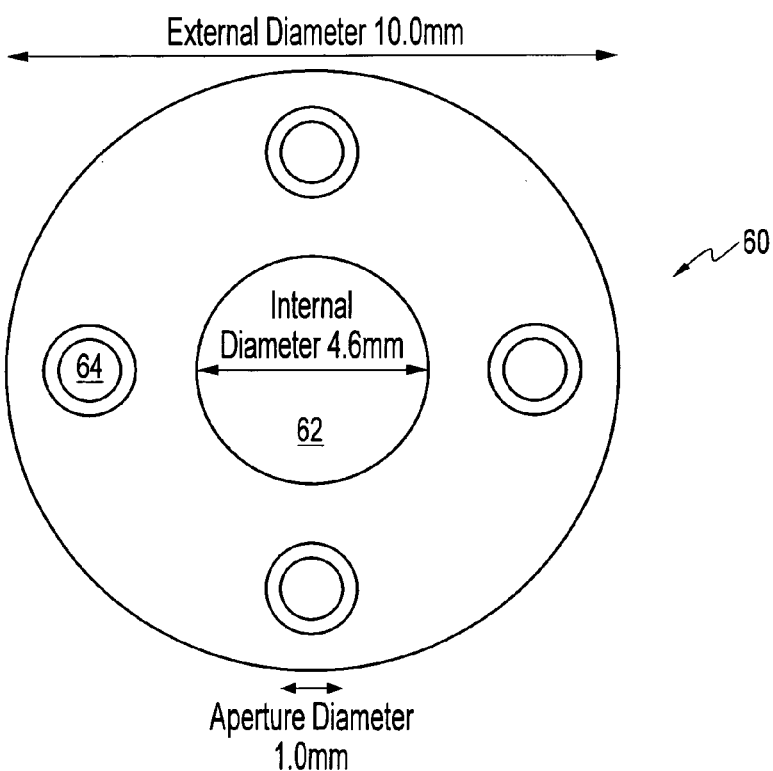

Reference is now made to FIGS. 5 and 5a which illustrate a first or second suture anchor in the form of a washer 60. In the illustrated embodiment, the washer 60 has an external diameter of about 10.0 mm. While the illustrated washer is disc-shaped, the washer is not so limited. The washer 60 is preferably formed from titanium or stainless steel although, as will be appreciated by those skilled in the art, any other suitable material, in particular any suitable bioabsorbable materials, may be used. The washer 62 also has at least two flexible coupling-locating apertures 64. In the illustrated embodiment, there are four apertures 64 circumferentially arranged about the aperture 62. In the illustrated embodiment, each of the apertures 64 has a diameter of about 1.0 mm. Each of the apertures 64 have beveled edges, above and below, while the aperture 62 has beveled edges above.

The washer 60 also has a substantially centrally located bone screw-retaining aperture 62. In the illustrated embodiment, the aperture 62 has a diameter of about 4.6 mm and the washer 60 is adapted to allow mobile positioning against an arcuate undersurface 69 of the head of the bone screw 68 (illustrated in FIG. 5b).

Figure 5B:
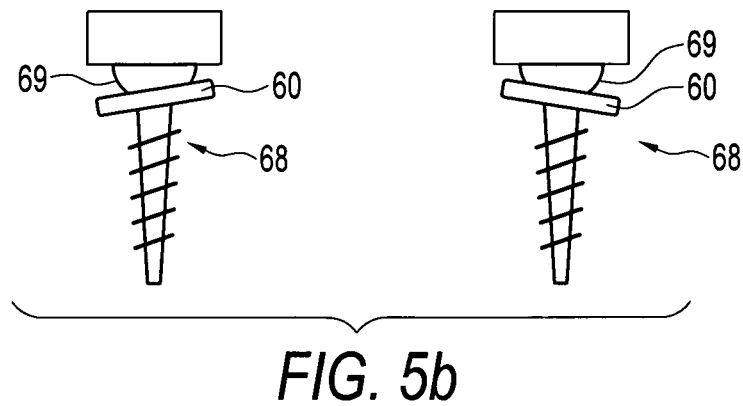
FIG. 5b illustrates the mobile positioning of the washer against an arcuate undersurface of the screw-head of a bone anchor.

Referring to FIGS. 5 and 5a, the washer 60 of the fourth aspect of the present invention is provided with a screw-retaining aperture 62 and at least two flexible coupling-locating apertures 64 which are preferably countersunk so as to allow easier threading passage of the flexible coupling 70 (not shown in FIGS. 5-5b). Care needs to be taken in such countersinking, to avoid compromising the mechanical strength of the apertures 62, 64 of the washer 60.

Figure 6:
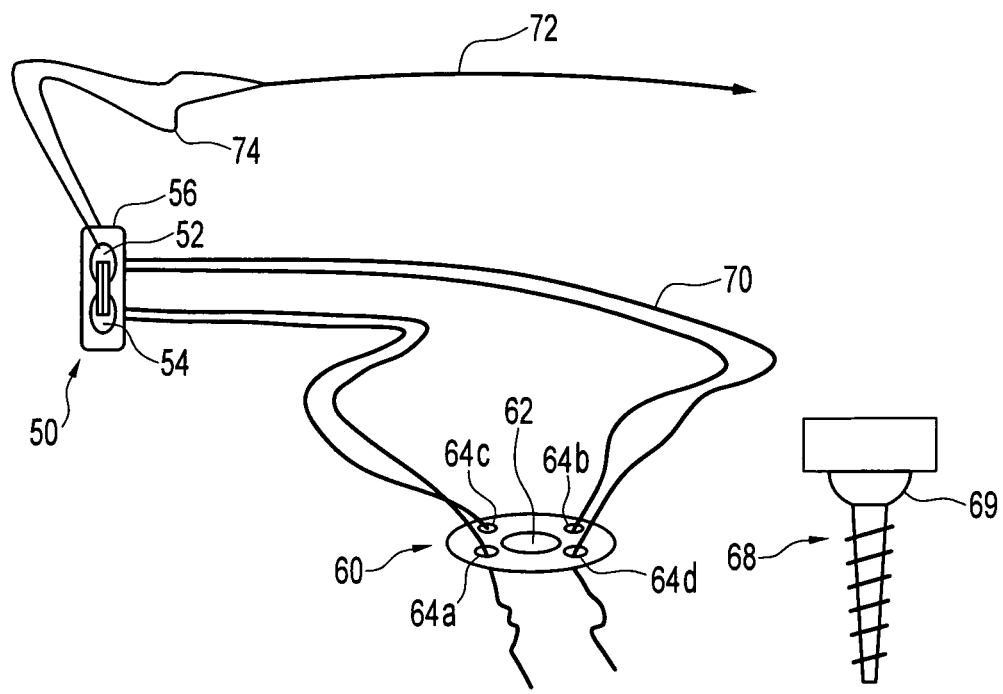
FIG. 6 shows a perspective view of the kit of parts comprising an apparatus of the present invention.

FIG. 6 illustrates the implant apparatus used for fixation of the AC joint dislocation. The button 50 and the washer 60 are secured or pre-threaded together by means of a flexible coupling in the form of first suture 70, preferably of number 5-strength braided polyester, which is double looped through the first and second apertures 52, 54 of the button 50 and the peripheral apertures 64 of the washer 60, as will now be described in greater detail. Specifically, the first suture 70 is fed through to aperture 64a of the washer 60; through the second and first apertures 54, 52 of the button 50; through the aperture 64b, under the washer 60 and back out the aperture 64c; through the second and first apertures 54, 52 of the button 50 again; and finally through the aperture 64d of the washer 60. A needle 72, which may be straight or curved, with a second, pull-through suture 74 is also looped through either the first or second apertures 52, 54 of the button 50. The second suture 74 is looped through the first aperture 52 of the button 50.

The first suture 70 used in the apparatus can be made from any material which is suitable for this purpose, whether absorbable or non-absorbable, provided it is sufficiently strong. A number 5-strength braided polyester (FIBER-WIRE®) suture is preferred. This is a non-absorbable suture which knots easily without slipping. The second suture 74 can be made from any material which is suitable for this purpose, and preferably should be at least 0-strength.

The pull through needle 72 can be of any dimensions, provided it is long enough to span the clavicle 12 or the coracoid process 14 of the shoulder 10. The needle 72 is preferably about 100 mm in length. The needle's body can either be straight or curved. The needle's tip can be either "taper cut" or "cutting."

In the present embodiment, leading and trailing edges of the button 50 are substantially symmetrical, although it will be appreciated that this is not a requirement of the present invention. Specifically, the leading edge 56 (illustrated in FIG. 6) of the button 50 should be blunt and should have a width sufficient to reduce the possibility that the leading edge 56 of the button 50 follows the second or pull-through suture 74 through the intact skin or to catch or skewer any soft tissue structures between the bone and the skin, as will be described in detail hereinafter.

Figure 7A:
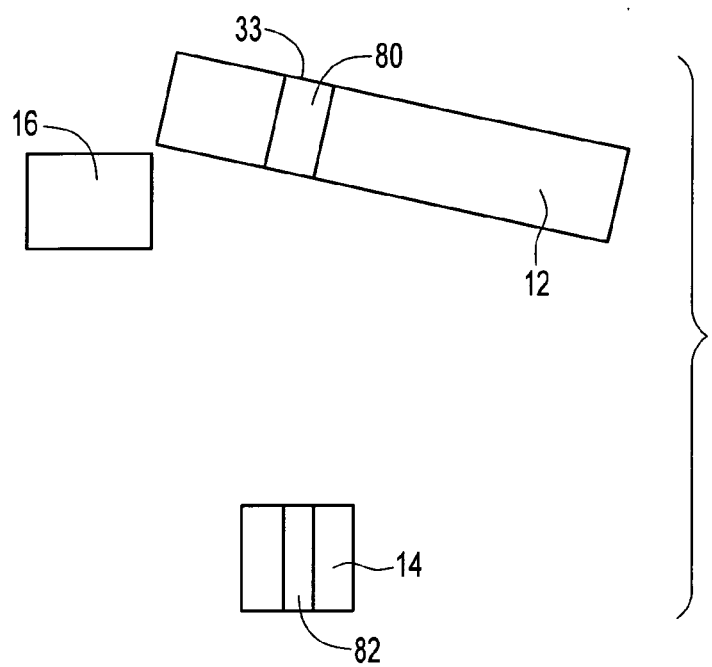
FIGS. 7a-7f illustrate, in sequence, the steps of a method according to the present invention.

FIG. 6 also illustrates a bone screw 68 as part of the implant apparatus. The bone screw 68 is used for engaging the washer 60 with the coracoid process 14 (FIG. 7f). As discussed below in detail and with reference to FIG. 5b, the bone screw 68 has an arcuate undersurface 69 for defining the movement of the washer 60 between the coracoid process 14 and the arcuate undersurface 69.

TABLE 1

| Apparatus/Button of FIGS. 3 and 6 | |
|---|---|
| Button 50 overall dimensions: | 10.0 mm (length) × 3.5 mm (width) × 1.5 mm (thickness) |
| Basic shape: | Oblong in plan shape, with chamfered or rounded corners and edges - this reduces the chance of the button 50 being palpated under the skin and, in addition, eases the passage of the button 50 through a drill hole as will be explained hereinafter. |
| Button 50 material: | Preferably titanium or stainless steel |
| Button apertures 52, 54: | Two apertures 52, 54 (oblong in plan shape) |
| Apertures 52, 54 dimensions: | 2 mm height × 3 mm length (oblong with chamfered edges), preferably 1 mm distance between first and second apertures |
| Suture 70 (first suture): | Number 5-strength braided polyester suture, looped twice through the first and second apertures 52, 54 of the button 50 and each of the four peripheral apertures 64 (64a, 64b, 64c, 64d) of the washer 60, leaving the two free ends of suture 70 free for tying adjacent the undersurface of the washer 60. |
| Pull-through needle 72: | 100 mm long straight, or curved, needle 72 with pull-through, or second suture 74 attached. |
| Pull-through suture 74: | Minimum 0-strength suture 74 looped through the aperture 52 of the button 50, second suture 74 being secured to needle 72. |

The following sets out the procedure, as shown in FIGS. 7a-7f, to be followed for Rockwood Type III dislocations. Surgeons skilled in the art will appreciate the modifications that might be needed in addressing Rockwood Type II and IV-VI dislocations.

Set-Up

The patient is positioned in a "deck-chair" position on the operating table (not shown). A sandbag (not shown) can be placed under the scapula to ease access to the shoulder region. A longitudinal or horizontal incision of about 5 cm is made on the skin, at the front of the shoulder, overlying the coracoid process 14 and the clavicle 12. The clavicle 12 and the superior surface of the coracoid process 14 are exposed by blunt dissection. As explained in detail below, if the clavicle hole 80 is to be drilled (FIG. 7a) from above and substantially downwardly through the clavicle 12, it will also be necessary to retract the skin about the clavicle 12, in order to expose the superior surface 33 of the clavicle 12.

Instrumentation

A 3.5 mm drill bit is required for drilling a hole 80 through the clavicle 12. A 2.5 mm drill bit is required for drilling a hole 82 into the base of the coracoid process 14 of the scapula (FIG. 7a). It is not necessary that the drill holes 80, 82 be aligned with each other. In addition, it is not necessary, when the coracoclavicular interspace is reduced to normal, that the longitudinal axes of the respective drill holes 80, 82 be co-linear or even substantially parallel with each other.

Button Placement

Figure 7B:
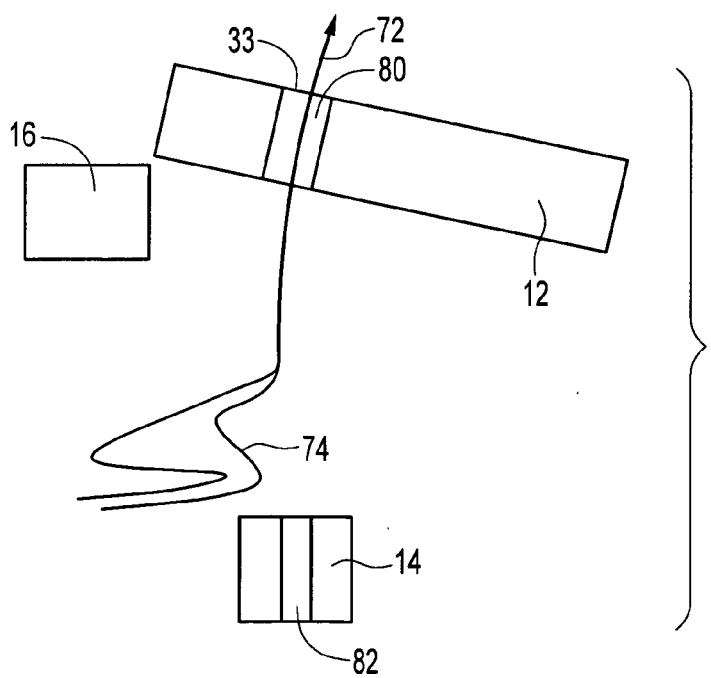
Figure 7C:
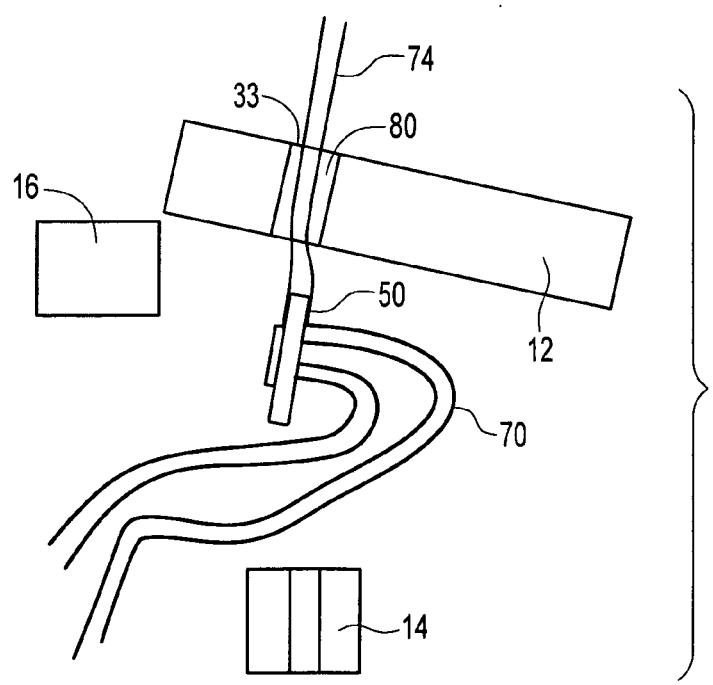

As illustrated in FIG. 7b, the long straight needle 72 with pull-through, second suture 74 is passed upwards through the 3.5 mm drill hole 80 in the clavicle 12 and can be passed through the intact skin on the superior aspect of the clavicle 12 or through the open surgical wound. In FIG. 7c, the pull-through suture 74, which engages the first aperture 52 (not shown) of the button 50, can now advance the button 50, substantially longitudinally through the drill hole 80. Engagement of the second suture 74 in the aperture 52 (not shown) ensures that the second suture 74 is located adjacent the longitudinal mid-line of the button 50 so that the second suture 74 stays central in the first aperture 52.

Figure 7D:
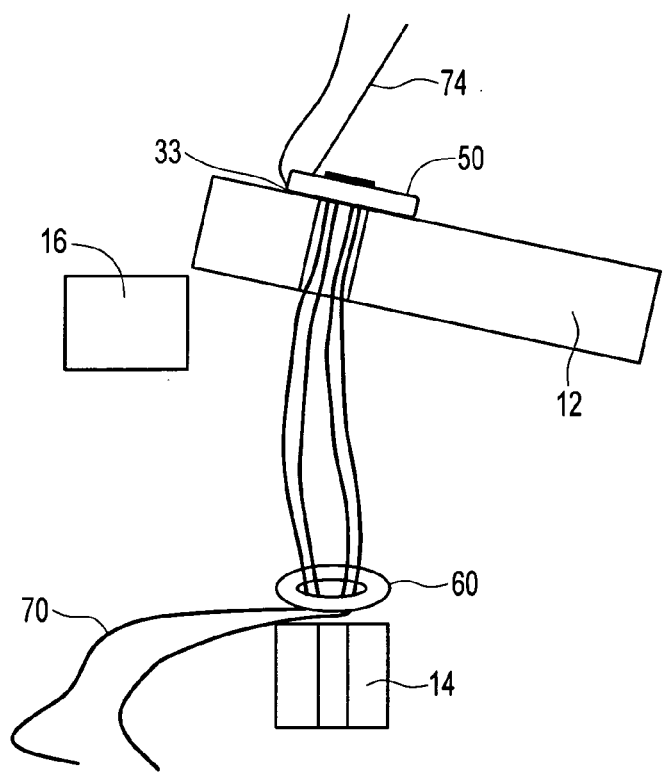
Figure 7E:
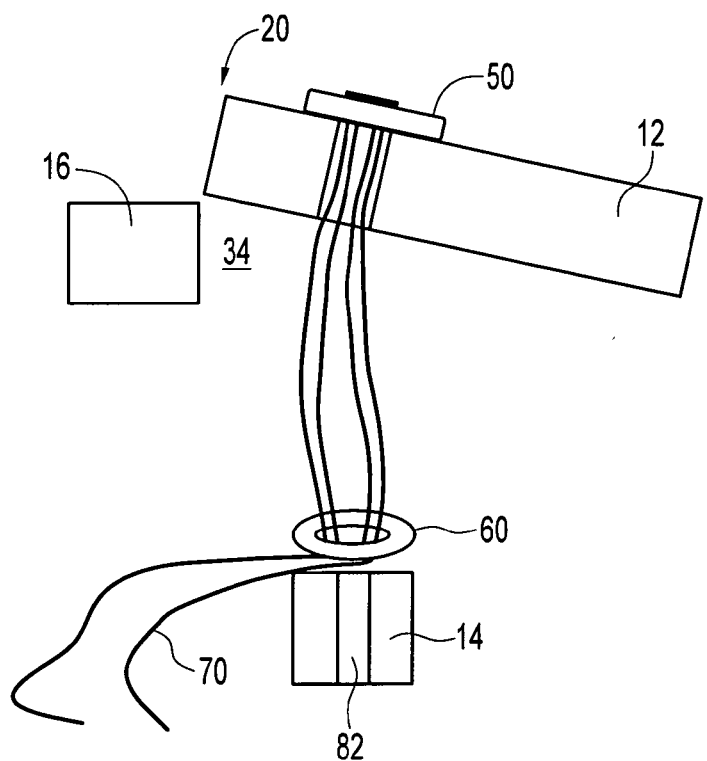
Figure 7F:
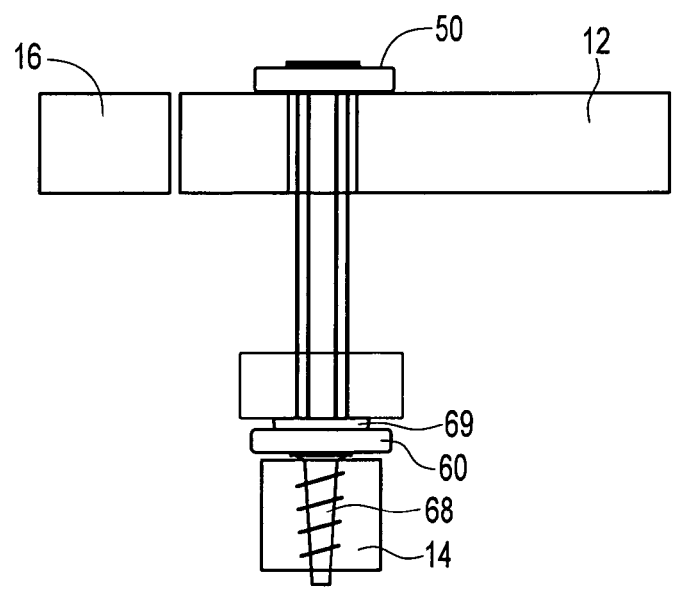

In FIG. 7d, once the button 50 has exited the superior surface 33 of the clavicle 12, the angle of traction on the pull-through, or second, suture 74 is changed and counter-traction is exerted on the first suture 70, in order to flip (pivot) the button 50 and engage the button 50 against the superior surface 33 of the clavicle 12. Once the button 50 is anchored, the pull-through, or second, suture 74 can be cut and removed (FIGS. 7d and 7e). In FIG. 7f, the screw 68 containing the washer 60 is inserted into the 2.5 mm drill hole 82 (FIG. 7e) in the base of the coracoid process 14 of the scapula. Before the washer 60/bone screw 68 is fully seated into the drill hole 82, the acromioclavicular joint 34 is reduced by downward manual pressure on the lateral end 20 of the clavicle 12 (FIGS. 7e and 7f).

The two trailing ends of the first suture 70 (FIG. 7e) are pulled to approximate the desired distance between the button 50 and the washer 60, and hence reduce the interval between the clavicle 12 and the coracoid process 14. The first suture 70 is then secured to itself with a knot, tied tight by hand. The free ends of the first suture 70 can then be cut approximately 1 cm long, to avoid knot slippage. The screw 68 can then be fully seated into the drill hole 82 in the coracoid process 14 to maximize suture tension, or may be advanced or retracted accordingly to fine tune the suture tension, according to the surgeon's preference.

The volume between the arcuate undersurface 69 of the bone screw 68 and the coracoid process 14 defines the maximum flexibility of the washer 60 therebetween. The designed flexibility is helpful in increasing the tolerance for non-aligned drill holes and the like.

Post-Operative Management

Following wound closure, the shoulder should be placed in a shoulder immobilizer for three weeks. Gentle range of motion exercises can begin after three weeks. Full range exercises can be allowed after six weeks.

Implant Removal

Routine removal of the first suture anchor-suture-second suture anchor construct is not required. If, for any reason, it needs to be removed, this can be performed simply by re-opening the surgical incision, cutting the first suture 70 as it loops through the button 50 and removing the button 50. The screw 68 and washer 60 can be removed easily using the screwdriver.

It is noted that the above description and drawings are exemplary and illustrate preferred embodiments that achieve the objects, features and advantages of the present invention. It is not intended that the present invention be limited to the illustrated embodiments. Any modification of the present invention which comes within the spirit and scope of the following claims should be considered part of the present invention.

What is claimed as new and desired to be protected by Letters Patent of the United States is:

1. A method for internal fixation of joint dislocations, the method comprises the steps of:
   providing an apparatus comprising: an oblong button; a suture anchor; and a flexible coupling that is double looped and extends between the oblong button and the suture anchor, one loop of the flexible coupling extends through apertures in the oblong button and another loop of the flexible coupling extends through apertures in the suture anchor, wherein the flexible coupling includes free ends located at a common side of one of the oblong button and the suture anchor;
   drilling first and second holes through respective portions of the joint dislocation;
   passing the oblong button with the flexible coupling through the first hole;
   pivoting the oblong button so as to engage the oblong button against a superior surface of the respective portion of the first hole;
   securing the suture anchor at the second hole to engage a superior aspect of the respective portion of the second hole; and
   reducing and fixing the distance between the oblong button and the suture anchor by traction of the flexible coupling extending between the oblong button and the suture anchor.

2. The method according to claim 1, in which the reducing step is carried out before the step of securing the suture anchor.

3. The method according to claim 1, in which the apparatus is also provided with a needle that is flexibly attached to the oblong button which is subsequently uncoupled from the oblong button, after the oblong button has been advanced through the hole.

4. The method according to claim 1 comprises: fixing acromioclavicular joint dislocations, wherein the respective portions are the clavicle and the coracoid.

5. The method according to claim 4, wherein the engaging step includes flipping the oblong button to position the oblong button against a superior surface of the clavicle.

6. The oblong button for use in the method according to claim 1, wherein the apertures comprise first and second apertures which are oblong, a longitudinal mid-line of the respective oblong apertures being located substantially about a longitudinal mid-line of the oblong body.

7. The button according to claim 6, in which the button has a width in the range of about 2.5 mm to about 4.0 mm.

8. The button according to claim 6, in which the button has a width in the range of about 3.25 mm to about 4.0 mm.

9. The button according to claim 6, in which the button has a length in the range of about 7.5 mm to about 12.5 mm.

10. The button according to claim 6, in which the button has a length in the range of about 9 mm to about 11 mm.

11. The suture anchor for use in the method according to claim 1, which comprises a washer body adapted for engagement with a bone anchor, the washer having at least two peripheral apertures.

12. The washer according to claim 11 in which the bone anchor is a bone screw and the body defines at least one screw-retaining aperture and at least two peripheral apertures is at least four peripheral apertures.

13. The washer according to claim 11, in which the washer has a diameter in the range of 8 mm to 14 mm.

* * * * *